United States Patent [19]
London et al.

[11] Patent Number: 5,969,144
[45] Date of Patent: Oct. 19, 1999

[54] RADIOLABELED PYRIDYL-7-AZABICYCLO [2,2,1]HEPTANES

[75] Inventors: Edythe D. London, Baltimore; Alane S. Kimes, Perry Hall; Andrew Horti, Columbia; Robert F. Dannals, Sparks, all of Md.; Michael Kassiou, Marrickville, Australia

[73] Assignee: The United States of America as represented by the Department of Health and Human Services, Washington, D.C.

[21] Appl. No.: 08/980,606

[22] Filed: Dec. 1, 1997

Related U.S. Application Data

[62] Division of application No. 08/642,636, May 3, 1996, Pat. No. 5,726,189.

[51] Int. Cl.$^6$ .................................................. C07D 401/04
[52] U.S. Cl. .................................................. 546/276.7
[58] Field of Search .................................................. 546/276.7

[56] References Cited

U.S. PATENT DOCUMENTS

| | | | |
|---|---|---|---|
| 3,932,429 | 1/1976 | Takeda et al. | 24/366 |
| 4,499,099 | 2/1985 | Watts | 514/299 |
| 4,985,063 | 1/1991 | Fischer et al. | 514/256 |
| 5,015,655 | 5/1991 | Galliani et al. | 514/413 |
| 5,314,899 | 5/1994 | Daly et al. | 514/339 |
| 5,462,956 | 10/1995 | Daly et al. | 514/397 |

FOREIGN PATENT DOCUMENTS

| | | |
|---|---|---|
| 7010878 | 1/1995 | Japan . |
| 7033771 | 2/1995 | Japan . |
| WO 94/22868 | 10/1994 | WIPO . |

OTHER PUBLICATIONS

CA 123: 246612, Houghtling et al., 1995.
CA 122: 309826, Alane et al., 1995.
CA 120: 77489, Corey et al., 1993.
CA 120: 315194, Badio et al., 1994.
Badio et al., Epibatidine, a Potent Analgetic and Nicotinic Agonist; *Molecular Pharmacology*, 45:563–56 (1994).
Dagami, Ron, Cocaine Analog for Parkinsonism Studies, *Chem& Eng. News*, pp. 25–26, Oct. 14, 1991.
Horti et al., *Chemical Abstracts*, 125:11186, 1996.
Imaging Alzheimer's, *Science*, 266:1810, Dec. 16, 1994.
Laruelle, Marc, et al., SPECT Imaging of Dopamine and Serotonin Tramporters with [1231]–2β–CIT Pharmacological Characterization of Brain Uptake in Nonhuman Primates, *Synapse, 13*: 295–309, (1993).
London et al., Nicotinic Binding Sites in Cerebral Cortex and Hippocampus in Alzheimer's Dementia *Neurochemical Research*, 14:745–750 (1989).
London et al., In vivo labeling of nicotinic acetylcholine receptors in brain With [$^3$H]epibatidine; *Europea Journal of Pharmacology*, 278 (1995) R1–R2.
Lundykvist, Camilia et al., [O–Methyl–$^{11}$C]β–CIT–FP, a Potential Radioligand for Quantitation of th Dopamine Transporter: Preparation, Autoradiography, Metabolite Studies, and Positron Emissio Tomography Examinations, *Nucl. Med. Biol.*, 22:905–913 (1995).
Neumeyer, John L., et al., [$^{123}$I]–2β–Carbomethoxy–3β–(r–iodophenyl)tropane: High–Affinity SPEC Radiotracer of Monoamine Reuptake Sites In Brain, *J. Med. Chem.*, 34:3144–3146 (1991).
Nybäck et al., Attempts to visualize nicotine receptors in the brain of monkey and man by positron emissio tomography; *Progress In Brain Research*, Nordberg et al. (ED.), 79:313–19 (1989).
Patt et al., [$^{11}$C]–N–methyl– and [$^{18}$F] fluoroethylepibatidine: Ligands for the Neuronal Nicotinic Receptor *Journal of Labelled Compounds and Radiopharmaceuticals, 37*: 355–56 (1995)(abstract only).
Siebyl, John P., et al., Reproducibility of Iodine–123–β–CIT SPECT Brain Measurement of Dopamin Transporters, *J. of Nuclear Med.*, 37:222–228, (1996).
Warpman et al., *Chemical Abstracts*, 124:199570, 1996.

*Primary Examiner*—Jane Fan
*Attorney, Agent, or Firm*—Leydig, Voit & Mayer, Ltd.

[57] ABSTRACT

The present invention is directed to radiolabeled epibatidine analogues, specifically FPH labeled with radioisotopes of fluorine and/or carbon. These radiolabeled epibatidine compounds are used to noninvasively image and quantify nicotinic cholinergic receptors in the living brain for both research studies and the diagnosis of neurodegenerative diseases.

13 Claims, No Drawings

RADIOLABELED PYRIDYL-7-AZABICYCLO [2,2,1]HEPTANES

This is a divisional of application Ser. No. 08/642,636, filed on May 3, 1996 now U.S Pat. No. 5,726,189.

FIELD OF THE INVENTION

The present invention is directed to epibatidine derivatives, and more particularly, to radiolabeled epibatidine analogues and methods of imaging and quantifying nicotinic acetylcholinergic receptors in the brain using radiolabeled epibatidine analogues.

BACKGROUND OF THE INVENTION

The nicotinic acetylcholine receptors are a major class of excitatory receptor in the brain. As such, they are important in normal physiology and in neuropathological states. Study of these receptors is important for research and diagnosis of neurodegenerative diseases. For example, the nicotinic acetylcholine receptor has been implicated in various neuropathological and physiological states, including Alzheimer's disease and addiction to tobacco products. With respect to tobacco addiction, these receptors are the sites at which the addictive drug nicotine produces its effects. However, in patients who have died from Alzheimer's disease, the densities of nicotinic acetylcholine receptors in the brain are reduced. Currently, Alzheimer's disease is definitively diagnosed only at autopsy, and rates of false positive diagnoses in living patients range from 19% to 45%. *Science*, 266, Dec. 16, 1994. A noninvasive method of diagnosing neurodegenerative diseases in the living human brain is highly desirable.

To date, an appropriate agent for labeling and quantifying the nicotinic acetylcholine receptors in living human brain is not available. These receptors have been characterized heretofore by radioligand binding and electrophysiological assays. Sargent, *Annu. Rev. Neurosci.*, 16:403 (1993). However, in vivo imaging studies of nicotinic acetylcholine receptors have been impeded by lack of a suitable radioligand.

The prior art discloses attempts to image neuroreceptor populations in living animals using various labeled compounds. However, until now, none of the labeled compounds have been successful in imaging and quantifying nicotinic acetylcholine receptors in the living brain.

For example, radiolabeled nicotine has been prepared and evaluated as a ligand for localizing and quantifying nicotinic cholinergic receptors ("nAChRs") by Positron Emission Tomography ("PET"), but its rapid clearance and relatively low affinity have limited its usefulness. Recent studies in mice have used labeled cytisine, another ligand with high affinity for nAChRs. Those studies indicate that this ligand does not clear as rapidly from the brain as nicotine and does not have as much non-specific binding. Both radiolabled nicotine and cytisine present limitations as in vivo tracers due to their non-specific binding in the brain and rapid clearance from the brain.

Recently, epibatidine has been discovered and various pharmacological uses for it have been suggested. Epibatidine (exo-2-(2-chloro-5-pyridyl)-7-azabicyclo[2.2.1] heptane), an extract of frog skin, has recently been discovered to produce antinociception, indicating central activity after peripheral administration, and extremely high potency for central nAChRs in vitro. Badio, *Mol. Pharmacol.*, 45:563 (1994). Epibatidine is disclosed U.S. Pat. Nos. 5,314,899 and 5,462,956. However, these patents do not disclose fluorine as a specific substituent. PCT application WO94/22868 to Shen et al. discloses the epibatidine analogue (±)-exo-2-(2-fluoro-5-pyridyl)-7-azabicyclo[2.2.1] heptane ("FPH") for its analgesic activity. Methods for preparing epibatidine may found in JP 702087 and JP 7033771.

Previously, epibatidine has been studied for use as an analgesic and nicotinic agonist. It has been learned that enantiomers of epibatidine have similar inhibition of nicotine binding to nicotinic sites in rat brains. *Mol. Pharmacol.*, 45:563–69 (1994).

Other labeled compounds, other than FPH, have been studied for use as ligands for the neuronal nicotinic receptor, for example, [$^{11}$C]N-methylepibatidine and [$^{18}$F] fluoroethylepibatidine, *Journal of Labelled Compounds and Radiopharmaceuticals*, 37:355–56 (1995), and nicotinic binding assays on the brains of patients who died of dementia of the Alzheimer type have been performed using [$^{3}$H] acetylcholine and [$^{3}$H]nicotine as radioligands. *Neurochemical Research*, 14:745–50 (1989).

Attempts have been made to visualize nicotinic receptors in the brain of monkey and man using PET and labeled nicotine as a ligand for the receptors. *Progress in Brain Research*, Nordberg et al. (Ed.), 79:313–19 (1989).

None of the prior art discloses a successful noninvasive method for imaging nAChRs in the living brain. Most prior methods could not be performed on living brain tissue. Although both nicotine and cytisine have been used in the living brain, they have been unsuccessful due to their non-specific binding affinity and their rapid clearance from the brain.

Despite the various compounds and methods disclosed in the prior art, there remains a need for a noninvasive method of imaging and quantifying nAChRs in the living human brain, to allow for research studies and the diagnosis of neurodegenerative diseases, including, for example, Alzheimer's disease.

SUMMARY OF THE INVENTION

The present invention provides appropriately radiolabeled epibatidine analogues, specifically FPH labeled with positron emitting radioisotopes of fluorine [$^{18}$F] and/or carbon [$^{11}$C]. The radiolabeled epibatidine analogues in accordance with this invention are administered to a mammal, and the presence of the compound in the mammal, especially the brain, is imaged and desirably quantified by positron emission tomography (PET), so as to indicate the presence and quantity of the nAChRs. The compounds are useful for imaging and quantifying nAChRs in human subjects by PET. The structure of the epibatidine molecule presents sites for introduction of $^{11}$C or $^{18}$F in the synthesis of radioligand probes especially suited for PET.

The present invention also provides epibatidine analogues radiolabeled with positron emitting radioisotopes of iodine [$^{123}$I]. These analogues are also administered to a mammal and its presence in the brain of the mammal is imaged and quantified by single photon emission computed tomography (SPECT) to indicate the presence and quantity of nAChRs, particularly in the brain.

DETAILED DESCRIPTION OF THE PREFERRED EMBODIMENTS

The present invention is directed to a method for imaging and quantifying nicotinic acetylcholinergic receptors in the brain of a mammal. The method comprises (a) administering to said mammal a compound of the formula:

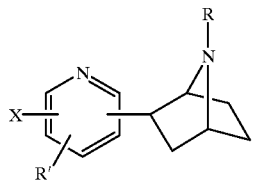

wherein R is selected from the group consisting of hydrogen, $C_1-C_6$ alkyl, halo $C_1-C_6$ alkyl, aryl, and aryl $C_1-C_6$ alkyl, R' is selected from the group consisting of hydrogen and $C_1-C_6$ alkyl, and X is selected from the group consisting of hydrogen, halo, and halo $C_1-C_6$ alkyl, wherein at least one of R, R' or X is radiolabeled, with the provisos that (i) when X is chloro, iodo, or alkyl and ortho to the pyridyl nitrogen and the azabicycloheptane moiety is para to X, R is aryl and aryl $C_1-C_6$ alkyl, and (ii) when X is hydrogen and the azabicycloheptane moiety is meta to the pyridyl nitrogen, R is not hydrogen; and (b) imaging and quantifying said compound in the brain of said mammal as indicative of the presence and quantity of said nicotinic acetylcholinergic receptors in the brain of said mammal.

The present invention is also directed to a compound of the formula

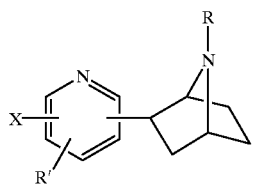

wherein R is selected from the group consisting of hydrogen, $C_1-C_6$ alkyl, halo $C_1-C_6$ alkyl, aryl, and aryl $C_1-C_6$ alkyl, R' is selected from the group consisting of hydrogen and $C_1-C_6$ alkyl, and X is selected from the group consisting of hydrogen and halo $C_1-C_6$ alkyl, wherein at least one of R or X is radiolabeled, with the proviso that when X is hydrogen and the azabicycloheptane moiety is meta to the pyridyl nitrogen, R is not hydrogen.

Where the term "alkyl" is used, either alone or within other terms, such as "halo $C_1-C_6$ alkyl" and aryl $C_1-C_6$ alkyl", the term "alkyl" embraces linear or branched radicals. Examples of alkyl include, but are not limited to, methyl, ethyl, n-propyl, isopropyl, n-butyl, isobutyl, sec-butyl, tertiary-butyl, n-pentyl, iso-pentyl, methylbutyl, dimethylbutyl, neopentyl, and n-hexyl.

The halogen atom is bromine, fluorine, chlorine or iodine, preferably fluorine. The term "aryl" embraces phenyl, substituted phenyl and naphthyl.

By radiolabel of R,R' and/or X, it is meant that, in the case of R and R', one of the carbon atoms is $^{11}C$ and, in the case of X, the halogen atom is the radioactive isotope. Preferably, X is $^{18}F$.

In accordance with the present invention, there is provided a method and agent for noninvasive imaging of nAChRs in the brain in vivo. For example, it has been found that in vivo in mice and in a baboon, the radiolabeled fluorinated analog of epibatidine binds to nAChRs with very high affinity and negligible non-specific binding. This compound is preferred.

As is known, the presently available nuclear medicine imaging procedures for human use are single photon emission computed tomography, SPECT, and positron emission tomography, PET. The preferred fluoro analog of epibatidine, (±)-exo-2-(2-[$^{18}F$]fluoro-5-pyridyl)-7-azabicyclo[2.2.1]heptane in accordance with the invention, is especially useful with PET. A further preferred compound is (±)-exo-2-(2-bromo-5-pyridyl)-N-[$^{11}C$]$CH_3$-7-azabicyco[2.2.1] heptane, that is, where R is [$^{11}C$]$CH_3$, R' is hydrogen and X is bromine. The compounds in accordance with the present invention are useful with PET. For an $^{123}I$ analog of epibatidine, SPECT is preferred. The present invention thus allows the study of the nAChRs to elucidate their function in the brain and to facilitate diagnosis of conditions that could be detected on the basis of alterations in the densities of nAChRs in the brain, such as neurodegenerative diseases, including Alzheimer's disease.

The compounds of the present invention may be administered by any suitable route, preferably in the form of a pharmaceutical composition adapted to such a route, and in a dose effective to image and desirably quantify the nAChRs in the brain. Preferably, the compounds are administered intravenously to minimize metabolism before the compound enters the brain. The amount of the compounds of the present invention required to image or quantify the nAChRs in the brain will be readily ascertained by one of ordinary skill in the nuclear medicine art taking into account the specific activity of the compound and the radiation dosimetry. As is known by those skilled in the nuclear medicine art, the number of milliCuries of the radiolabeled compounds to be administered for the PET or SPECT scan will be limited by the dosimetry, whereas the mass of compound to be administered (e.g. μg/kg or mg/kg of body weight of the patient) is calculated based on the specific activity of the synthesized compound, i.e., the amount of radioactivity/mass, of radiolabeled compound. It will be appreciated that because of the short half-life of the radioisotopes, e.g. about 2 hours for $^{18}F$ and about 20 minutes for $^{11}C$, it is often necessary to make the radiolabeled compound at or near the site of administration. For $^{123}I$, the half-life is slightly longer, being about 13 hours. The specific activity of the compounds must then be ascertained in order to calculate the proper dosing. Such techniques are well known to those skilled in the art.

By way of illustration, and not in limitation, it has been found that in mice, the microCuries of radioisotopes should be about 200 to 300, and in baboons the milliCuries should be about 5. In keeping with that determination, the injected mass of FPH should be less than 1 μg/kg. Further, for a radiolabeled FPH of 2000 milliCuries/micromole, about 5 millicuries of radiation should be administered to a 70 kg patient. It is preferable not to use a radiolabeled compound of less than 1500 milliCuries/micromole.

EXAMPLE 1

This example illustrates the preparation of (±)-exo-2-(2-[$^{18}F$]fluoro-5-pyridyl)-7-azabicyclo[2.2.1]heptane ("[$^{18}F$] FPH")

The radiochemical synthesis of (+/−)-exo-2-(2-[$^{18}F$] fluoro-5-pyridyl)-7-azabicyclo[2.2.1]heptane (FPH) was accomplished by Kryptofix(r) 222 assisted nucleophilic no-carrier-added [$^{18}F$] fluorination of (+/−)-exo-2-(2-bromo-5-pyridyl)-7-azabicyclo[2.2.1]heptane. In a 10 ml Reactivial, an aqueous solution of the $^{18}F$ (prepared by 16 MeV proton irradiation of 98% enriched $H_2^{18}O$) 0.20 mg of Kryptofix (r) 222, and 6 mg $K_2CO_3$ were heated under a stream of argon in an oil bath at 120° C. while water was azeotropically evaporated using repeated additions of dry acetonitrile. A solution of (+/−)-exo-2-(2-bromo-5-pyridyl)-7-azabicyclo[2.2.1]heptane, 5 mg) in anhydrous DMSO (0.5 ml) was added into the reaction vessel. The reaction vessel was sealed and heated at 190° C. for 15 minutes. The reaction mixture was cooled and diluted with 0.5 ml of preparative HPLC mobile phase and injected onto the Waters PrepPak μ Bondapak[al C 18 HPLC cartridge (25 mm×100 mm) and eluted with $CH_3CN:H_2O:CF_3COOH$ (15:85:0.15) at a flow rate of 12 ml/minute. The radioactive peak with a retention time of 7–8 min corresponding to unradioactive labelled [$^{18}$F] FPH was collected and the solvent was removed on rotary-evaporator. The product was redissolved in saline (5 ml) and $NaHCO_3$ (0.2–0.3, 8.4%) was added. The pH of the final solution was 6.0. An aliquot of the final solution of known volume and radioactivity was applied to an analytical reverse-phase HPLC column (Alltech Econosil C18 10 m 250 mm×4.6 mm). A mobile phase of CH, $CN:H_2O:CF_3COOH$ (12.5:87.5:0.15) at a flow rate of 3 ml/minute was used to elute the radioligand ($R_t$=4 minutes). The area of the UV absorbance peak measured at 254 nm corresponding to carrier product was measured and compared to a standard curve relating mass to UV absorbance. The sample also coeluted with unradioactive labelled FPH. The average radiochemical yield was 10%, the average specific activity was greater than 2000 mCi/μmol, calculated at the end-of-synthesis and radiochemical purity was greater than 95%.

This procedure was repeated multiple times using varying heating temperatures and amounts of $K_2CO_3$ and (±)-exo-2-(2-bromo-5-pyridyl)-7-azabicyclo[2.2.1]heptane. It is desirable to use about 2 to about 8 mg, preferably 5 or 6 mg of $K_2CO_3$ and preferably about 2 to 5 mg (±)-exo-2-(2-bromo-5-pyridyl)-7-azabicyclo[2.2.1]heptane. Further, the reaction may be carried out at temperatures between about 190° to 210° C., preferably 200° C.

EXAMPLE 2

The utility of [$^{18}$F] FPH as an agent to label, in vivo, nAChRs in mouse brain was tested. Mice received 0.4 μCi of [$^{18}$F]FPH (sp. act >2000 mCi/μmol) by tail vein injection. The regional distribution of the tracer in brain was assessed in the absence and presence of unlabeled epibatidine. [$^{18}$F] FPH showed a regional distribution similar to that of nAChRs. At 30 minutes post injection, uptake was highest in the thalamus (11% injected dose/g tissue (%ID/g) and in superior colliculus (10% ID/g), intermediate in cortex (6.2% ID/g) and hippocampus (6% ID/g) and lowest in cerebellum (<3% ID/g). Pretreatment with unlabeled epibatidine (20 μg/kg) reduced binding in all regions to ~3% ID/g). In in vitro assays, the Ki for unlabeled FPH against nAChRs labeled with [$^3$H] epibatidine was approximately 3 pM. The findings suggest that [$^{18}$F]FPH would be an excellent ligand for imaging nAChRs in living human brain.

EXAMPLE 3

An additional study in a baboon using [$^{18}$F]FPH as the agent to label and PET to image the nAChRs indicated that high densities of nAChRs were readily observed, particularly in the thalamus.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

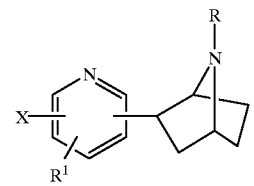

wherein R is selected from the group consisting of hydrogen, $C_1$–$C_6$ alkyl, halo $C_1$–$C_6$ alkyl, aryl, and aryl $C_1$–$C_6$ alkyl, $R^1$ is selected from the group consisting of hydrogen and $C_1$–$C_6$ alkyl, and X is selected from the group consisting of hydrogen, halo, and halo $C_1$–$C_6$ alkyl, wherein at least one of R, $R^1$, and X is radiolabeled.

2. The compound of claim 1, wherein said X is a halo.

3. The compound of claim 2, wherein said halo is fluoro.

4. The compound of claim 3, wherein said R is selected from the group consisting of hydrogen and $C_1$–$C_6$ alkyl.

5. The compound of claim 4, wherein said R is selected from the group consisting of hydrogen and methyl.

6. The compound of claim 5, wherein said R is hydrogen.

7. The compound of claim 5, wherein the azabicycloheptane moiety is para to X.

8. The compound of claim 7, wherein said compound is (+/−)-exo-2-(2-[$^{18}$F]fluoro-5'-pyridyl)-7-azabicyclo[2,2,1]-heptane.

9. The compound of claim 2, wherein said halo is bromo.

10. The compound of claim 9, wherein R is selected from the group consisting of hydrogen and $C_1$–$C_6$ alkyl.

11. The compound of claim 10, wherein said R is selected from the group consisting of hydrogen and methyl.

12. The compound of claim 11, wherein said R is methyl.

13. The method of claim 12, wherein said compound is (±)-exo-2-(2-bromo-5'-pyridyl)-N-[$^{11}$C]$CH_3$-7-azabicyclo[2,2,1]heptane.

* * * * *